Aug. 10, 1971 H. W. GUENGERICH Plant Pat. 3,057
APPLE TREE
Filed Aug. 15, 1969
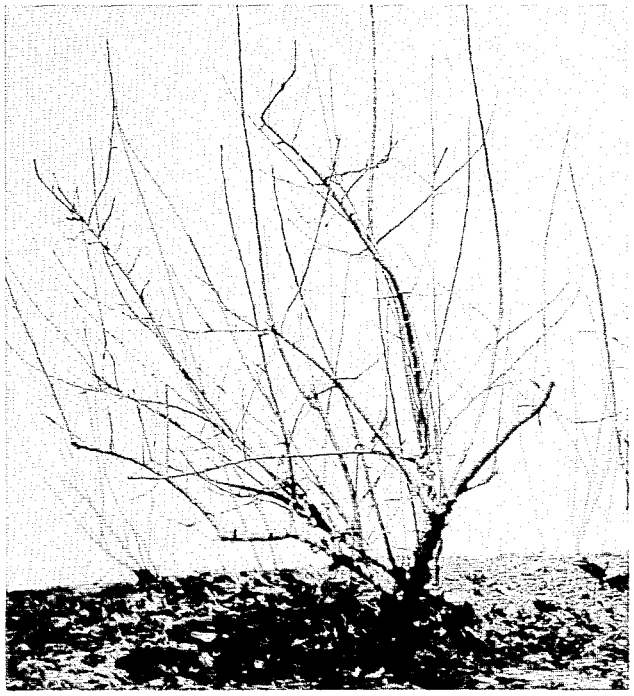
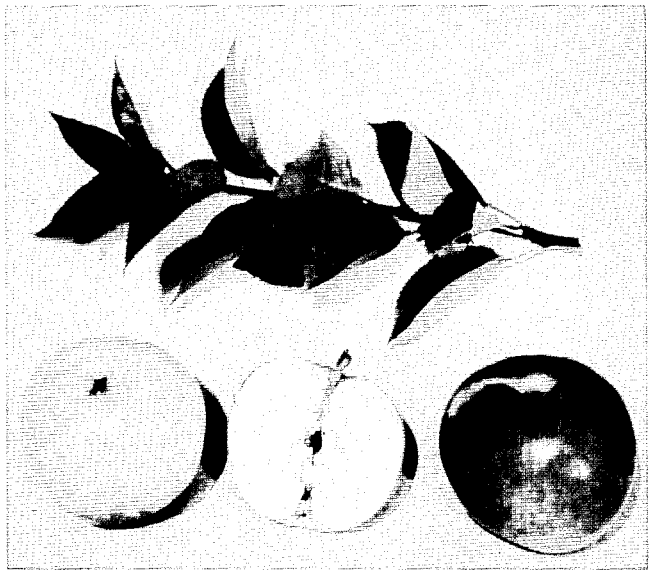
Inventor.
H. W. Guengerich
By: Robb & Robb
Attorneys.

United States Patent Office

Plant Pat. 3,057
Patented Aug. 10, 1971

3,057

APPLE TREE

Harry W. Guengerich, Louisiana, Mo., assignor to Stark Bro's Nurseries & Orchards Company, Louisiana, Mo.

Filed Aug. 15, 1969, Ser. No. 850,681
Int. Cl. A01h *5/03*
U.S. Cl. Plt.—34 1 Claim

The present invention relates to a new and distinct variety of apple tree which was discovered by me in a test orchard owned by my assignee and located near Louisiana, in Pike County, Mo., said new variety having originated as an open-pollinated seeedling of the variety of apple tree known as "Clark Dwarf" (unpatented).

My new discovery was the result of a research program conducted by my assignee under my direction, and which had for its primary objective the development of a new and improved variety of apple tree which would be useful as dwarfing interstock for producing dwarf apple trees having improved characteristics as compared with those produced by an unnamed and unpatented dwarfing interstock known as "EM VIII" which heretofore has been widely used by my assignee, but is susceptible to stem-pitting virus. This objective was fully achieved, as evidenced by the fact that although, as a tree, if resembles "EM VIII" in size, vigor and form, and produces dwarf trees similar to those produced by "EM VIII" when used as dwarfing interstock, the new variety is more tolerant to stem-pitting virus than the variety "EM VIII." In addition, dwarf trees produced by the use of my new variety as a dwarfing interstock, are only about half the size of standard trees grown to maturity on the usual seedling rootstock, but are caused to bear at an early age and heavily. All of these attributes are commercially valuable.

As exual reproduction of my new variety of layering, as performed by me in Pike County, Mo., shows that the foregoing characteristics and distinctions come true and are established and transmitted through succeeding propagations.

The accompanying drawing shows a typical bare tree of my new variety, as well as typical specimens of its foliage and fruit, with one of the fruit specimens being shown in longitudinal cross-section, and all as depicted in color as nearly true as it is reasonably possible to make the same in a color illustration of this character.

The following is a detailed description of my new variety, with color terminology in accordance with Ridgway's Color Standards and Nomenclature, hereinafter abbreviated as "R," and Horticultural Colour Guide, hereinafter abbreviated as "HCG," except where general color terms of ordinary dictionary significance are obvious:

Location where grown and observed: Pike County, Mo.

Dates of first and last pickings: About August 1 and August 15, respectively.

Tree: Small; medium vigorous; spreading; low; open; vase-formed; slow growing; hardy; very productive; regular bearer.

*Trunk.*—Stocky; shaggy.

*Branches.*—Medium slender. Color (shoots)—Diamine Brown, Plate XIII (Color No. 3', toner m (R).

*Lenticles.*—Numerous; medium small.

*Leaves.*—Medium large; wide; medium length; ovate; abruptly pointed; thick, smooth. Length—From 3 inches to 3½ inches. Width—From 2 inches to 2⅛ inches. Color—Spinach Green, Plate 0960, page 187, volume II, (HCG). Margin—Coarsely serrate. Petiole—Medium length (from ⅝ inch to ⅞ inch); medium thickness.

Flowers: Medium early; medium large.

*Dates of first and full bloom.*—About April 19 and April 27, respectively.

*Color.*—White, with pink tinge near margins of some petals.

Fruit:

*Maturity when described.*—Hard ripe (about August 7).

*Size.*—Variable. Axial diameter—about 2¼ inches. Transverse diameter—From about 2½ inches to 2¾ inches.

*Form.*—Globose-oblate; ribbed.

*Cavity.*—Unsymmetrical; apex acute; furrowed; lipped toward apex. Depth—Shallow (from about ¼ inch to ⅜ inch). Breadth—About ¾ inch. Markings—None.

*Basin.*—Unsymmetrical; flaring; furrowed; glabrous. Depth—From about ¼ inch to ⅜ inch. Breadth—about ¾ inch. Markings—None.

*Stem.*—Clubbed; stout; short. Length—From about 3/16 inch to ¼ inch. Breadth—About ⅛ inch. Markings—None.

*Calyx.*—Closed; segments persistent; broadly lanceolate; about 3/16 inch long; approximate at base; reflexed from base at apex; converged from base toward center; pubescent on both inner and outer surfaces.

*Skin.*—Thick; tough; smooth; glossy; waxed. Dots—Obscure; many; small; depressed; circular. Color—White. Distribution—over entire surface. Ground color—Sap Green, Plate 62/2, page 62, volume I (HCG). Color markings—blushed. Color—Carmine, Plate 21/1, page 21, volume I (HCG). Bloom—Wanting. Scarfskin—Wanting. General color effect—Bright Red, with yellowish-green ground color.

*Flesh.*—Rather dry. Color—White, with greenish tint. Texture—Firm; tough; fine; crisp. Flavor—Austere. Aroma—Wanting. Quality—Inferior.

*Core.*—Distant. Bundle area—Medium large; cordate; symmetrical. Halves of core—Equal. Bundles—Conspicuous; in one whorl. Color—Green. Core lines—Clasping. Cross-section—Indistinct. Carpellary area—Indistinct; large. Calyx tube—Glabrous toward base; apex cone-shaped. Entire depth—7/16 inch.

*Styles.*—Present; united toward base; pubescent throughout.

*Stamens.*—In one basal whorl.

*Seed cells.*—Axile; closed. Cell walls—Distant; thin; tough. Length—About 11/16 inch. Breadth—About ⅜ inch. Longitudinal section—Broadly oval; obtuse at apex. Surface—Entire; smooth. Cross-section—Broad.

Seeds:

*Average number.*—5 or 6 perfect and 3 imperfect; 2 per cell.

*Length.*—About 3/32 inch.

*Breadth.*—About 3/16 inch.

*Form.*—Obtuse.

*Color.*—Argus Brown, Color No. 13, tone m (R).

Use: Fruit worthless, but woody stems useful as good dwarfing interstock.

Disease resistance: Bood tolerance to stem-pitting virus, as determined by comparison with other varieties grown under comparable conditions in Pike County, Mo.

I claim:

1. A new and distinct variety of apple tree, substantially as herein shown and described, characterized particularly as to novelty by its general resemblance in size, vigor and form to the unnamed and unpatented variety identified as "EM VIII" formerly used extensively as dwarfing interstock, but having a greater tolerance to stem-pitting virue than "EM VIII," said new variety also having superior utility as dwarfing interstock to produce dwarf apple trees about half the size of standard trees grown on seedling rootstock, but which bear earlier and heavily.

No references cited.

ROBERT E. BAGWILL, Primary Examiner